United States Patent
Crapo et al.

(10) Patent No.: US 10,064,871 B2
(45) Date of Patent: Sep. 4, 2018

(54) METHODS OF TREATING SKIN DISORDERS

(71) Applicant: Biomimetix JV, LLC, Englewood, CO (US)

(72) Inventors: James D. Crapo, Englewood, CO (US); Kimberly C. Stone, Greenwood Village, CO (US)

(73) Assignee: BioMimetix JV, LLC, Englewood, CO (US)

( * ) Notice: Subject to any disclaimer, the term of this patent is extended or adjusted under 35 U.S.C. 154(b) by 0 days.

(21) Appl. No.: 15/109,157

(22) PCT Filed: Jan. 21, 2015

(86) PCT No.: PCT/US2015/012231
§ 371 (c)(1),
(2) Date: Jun. 30, 2016

(87) PCT Pub. No.: WO2015/112588
PCT Pub. Date: Jul. 30, 2015

(65) Prior Publication Data
US 2016/0324867 A1    Nov. 10, 2016

Related U.S. Application Data

(60) Provisional application No. 61/930,126, filed on Jan. 22, 2014.

(51) Int. Cl.
*A61K 31/555* (2006.01)
*A61K 31/409* (2006.01)

(52) U.S. Cl.
CPC .......... *A61K 31/555* (2013.01); *A61K 31/409* (2013.01)

(58) Field of Classification Search
CPC .......................... A61K 31/409; A61K 31/555
See application file for complete search history.

(56) References Cited

U.S. PATENT DOCUMENTS

| | | |
|---|---|---|
| 3,936,385 A | 2/1976 | Cheng |
| 4,257,433 A | 3/1981 | Kwan |
| 4,865,545 A | 9/1989 | La Rocca |
| 5,061,106 A | 10/1991 | Kent |
| 5,141,290 A | 8/1992 | Mairon |
| 5,152,686 A | 10/1992 | Duggan et al. |
| 5,223,537 A | 6/1993 | Stjernschantz et al. |
| 5,785,523 A | 7/1998 | Overmyer |
| 5,939,051 A | 8/1999 | Santalucia et al. |
| 5,968,480 A | 10/1999 | Bergeron et al. |
| 5,989,526 A | 11/1999 | Aaslyng et al. |
| 6,270,890 B1 | 8/2001 | Curtis et al. |
| 6,289,904 B1 | 9/2001 | Suhonen et al. |
| 6,372,727 B1 | 4/2002 | Crow et al. |
| 6,416,744 B1 | 7/2002 | Robinson et al. |
| 6,479,477 B1 | 11/2002 | Crapo et al. |
| 6,514,483 B2 | 2/2003 | Xu et al. |
| 6,583,132 B1 | 6/2003 | Crapo et al. |
| 6,592,849 B2 | 7/2003 | Robinson et al. |
| 6,680,299 B2 | 1/2004 | Or et al. |
| 6,680,322 B2 | 1/2004 | Or et al. |
| 6,680,324 B2 | 1/2004 | Castelhano et al. |
| 6,844,004 B2 | 1/2005 | Andersson |
| 6,916,799 B2 | 7/2005 | Fridovich et al. |
| 7,025,950 B2 | 4/2006 | Majeti et al. |
| 7,229,286 B2 | 6/2007 | Jones et al. |
| 7,251,849 B2 | 8/2007 | Moskovich et al. |

(Continued)

FOREIGN PATENT DOCUMENTS

| | | |
|---|---|---|
| WO | WO 97/35573 A2 | 10/1997 |
| WO | WO 00/43395 A1 | 7/2000 |

(Continued)

OTHER PUBLICATIONS

International Search Report and Written Opinion, PCT/US2015/012231, dated Apr. 7, 2015.
International Search Report and Written Opinion, PCT/US2015/012228, dated Apr. 10, 2015.
Batinic-Haberle et at. "Superoxide Dismutase Mimics: Chemistry, Pharmacology, and Therapeutic Potential" *Antioxidants & Redox Signaling* 13(6):877-918 (2010).
Batinic-Haberle et al. "Diverse functions of cationic Mn(III) N-substituted pyridylporphyrins, recognized as SOD mimics" *Free Radical Biology & Medicine* 51:1035-1053 (2011).

(Continued)

*Primary Examiner* — Zohreh A Fay
(74) *Attorney, Agent, or Firm* — Myers Bigel, P.A.

(57) ABSTRACT

A method of treating a skin disorder (e.g., an inflammatory or neoplastic skin disorder) in a subject in need thereof is carried out by administering (e.g., topically administering) the subject an active agent in a treatment effective amount. The active agent may be a compound of Formula I: wherein: each R is independently selected substituted or unsubstituted aryl, heteroaryl, cycloalkyl, or heterocycloalkyl; each A is an independently selected hydrogen, an electron-withdrawing group, or electron donating group; M is a metal; and $Z^-$ is a counterion; or a pharmaceutically acceptable salt thereof.

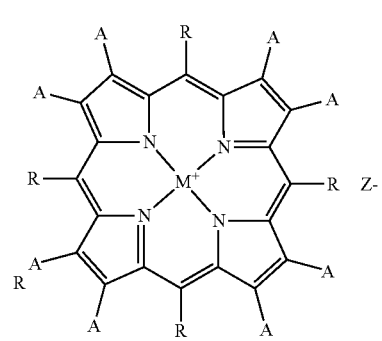

17 Claims, No Drawings

(56) References Cited

U.S. PATENT DOCUMENTS

| | | |
|---|---|---|
| 7,264,005 B2 | 9/2007 | Wong |
| 7,297,327 B2 | 11/2007 | Pilch et al. |
| 7,531,186 B2 | 5/2009 | Boeckh et al. |
| 7,976,854 B2 | 7/2011 | Hattendorf et al. |
| 8,003,636 B2 | 8/2011 | Wollmann et al. |
| 8,183,364 B2 | 5/2012 | Batinic-Haberle et al. |
| 8,211,656 B2 | 7/2012 | Hyde et al. |
| 8,217,166 B2 | 7/2012 | Salvemini et al. |
| 8,470,808 B2 | 6/2013 | Piganelli et al. |
| 8,486,928 B2 | 7/2013 | Riley |
| 8,513,305 B2 | 8/2013 | Davies |
| 2001/0012856 A1 | 8/2001 | Parks et al. |
| 2003/0229065 A1 | 12/2003 | Levy et al. |
| 2004/0023941 A1 | 2/2004 | Crapo et al. |
| 2010/0267825 A1 | 10/2010 | Malfroy-Camine |
| 2011/0184016 A1 | 7/2011 | Lerner et al. |
| 2011/0262511 A1 | 10/2011 | Love et al. |
| 2012/0065181 A1 | 3/2012 | Warner et al. |
| 2013/0195985 A1 | 8/2013 | Lepelletier et al. |
| 2016/0113940 A1 | 4/2016 | Crapo et al. |
| 2016/0324868 A1 | 11/2016 | Ji et al. |

FOREIGN PATENT DOCUMENTS

| | | |
|---|---|---|
| WO | WO 2008/129000 A1 | 10/2008 |
| WO | WO 2013/071059 A1 | 5/2013 |

OTHER PUBLICATIONS

Garibyan et al. "Understanding the pathophysiology of itch" *Dermatologic Therapy* 26(2):1-13 (2013).

Huynh, Tu T. "Burden of Disease: The Psychosocial Impact of Rosacea on a Patient's Quality of Life" *American Health & Drug Benefits* 6(6):348-354 (2013).

Li et al. "The Role of Manganese Superoxide Dismutase in Inflammation Defense" *Enzyme Research* 2011:1-6 (2011).

Liu et al. "Oxidative stress induces itch via activation of transient receptor potential subtype ankyrin 1 (TRPA1) in mice" *Neuroscience Bulletin* 28(2):145-154 (2012).

Mathur et al. "Physical and chemical penetration enhancers in transdermal drug delivery system" *Asian Journal of Pharmaceutics* 4(3):173-183 (2010).

Miriyala et al. "Manganese superoxide dismutase, MnSOD and its mimetics" *Biochimica Biophysica Acta* 1822:794-814 (2012).

Pathan et al. "Chemical Penetration Enhancers for Transdermal Drug Delivery Systems" *Tropical Journal of Pharmaceutical Research* 8(2):173-179 (2009).

Roosta et al. "Skin Disease and Stigma in Emerging Adulthood: Impact on Healthy Development" *Journal of Cutaneous Medicine and Surgery* 14(6):285-290 (2010).

Makinde et al. "Effect of a Metalloporphyrin Antioxidant (MnTE-2-PyP) on the Response of a Mouse Prostate Cancer Model to Radiation" *Anticancer Research* 29:107-118 (2009).

Musk et al. "Chemical Countermeasures for the Control of Bacterial Biofilms: Effective Compounds and Promising Targets" *Current Medicinal Chemistry* 13:2163-2177 (2006).

Oberley-Deegan et al. "The Antioxidant Mimetic, MnTE-2-PyP, Reduces Intracellular Growth of *Mycobacterium abscessus*" *American Journal of Respiratory Cell and Molecular Biology* 41:170-178 (2009).

Rogers et al. "Tandem dispersion and killing of bacteria from a biofilm" *Organic & Biomolecular Chemistry* 7:603-606 (2009).

Tyle, Praveen "Iontophoretic Devices for Drug Delivery" *Pharmaceutical Research* 3(6):318-326 (1986).

METHODS OF TREATING SKIN DISORDERS

RELATED APPLICATIONS

This application is a 35 U.S.C. § 371 national phase entry of PCT Application PCT/US2015/012231, filed Jan. 21, 2015, and published in English on Jul. 30, 2015, as International Publication No. WO 2015/112588, and which claims the benefit of U.S. Provisional Patent Application Ser. No. 61/930,126, filed Jan. 22, 2014, the disclosure of each of which is incorporated by reference herein in its entirety.

FIELD OF THE INVENTION

The present invention concerns the treatment of skin disorders and topical formulations useful for the same.

BACKGROUND OF THE INVENTION

Skin disorders are widespread in the general population: For example, in the UK, it is estimated that about 24% of the population consult their general practitioner with a skin problem in any 12 month period (RCGP Curriculum 2010, Statement 3.21 *Care of People with Skin Problems* (revised 7 May 2014)). Skin diseases are often chronic. In addition, they are often highly visible to others, and can have a substantial social stigma. Indeed, the skin disorders are increasingly recognized has having a substantial impact on healthy development and overall quality of life (N. Roosta, *skin disease and stigma in emerging adulthood: impact on healthy development*, J. Cutan. Med. Surg 14(6): 285-90 (2010); T. Huynh, *Burden of disease: The psychosocial impact of rosacea on a patient's quality of life*, Am. Health Drug Benefits 6(6): 348-354 (2013). Accordingly, there is a need for new ways to treat and manage skin disorders.

SUMMARY OF THE INVENTION

A first aspect of the invention is a method of treating a skin disorder in a subject in need thereof, comprising topically administering said subject an active agent in a treatment effective amount, wherein said active agent is a compound of Formula I:

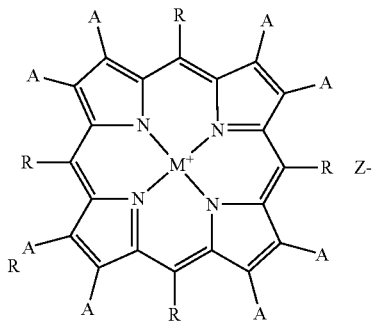

wherein:
each R is independently selected substituted or unsubstituted aryl, heteroaryl, cycloalkyl, or heterocycloalkyl;
each A is an independently selected hydrogen, an electron-withdrawing group, or electron donating group;
M is a metal; and
$Z^-$ is a counterion;
or a pharmaceutically acceptable salt thereof.

Non-limiting examples of skin disorders or conditions that may be treated by the methods and compositions described herein include, but are not limited to, inflammatory and neoplastic skin disorders. Particular examples include, but are not limited to, atopic dermatitis, psoriasis, contact dermatitis, seborrheic dermatitis, acne, radiation-induced skin inflammation (or radiation-induced skin fibrosis), radiation-induced mucositis (oral or gastrointestinal), basal-cell carcinoma of the skin, squamous-cell carcinoma of the skin, actinic keratosis, etc. (with additional examples being given below).

A further aspect of the invention is an active compound as described above or below for use in treating a skin disorder or condition as described above or below, or for the preparation of a medicament for use in treating a skin disorder or condition as described above or below.

The present invention is explained in greater detail in the specification set forth below. The disclosures of all United States patents cited herein are incorporated herein by reference.

DETAILED DESCRIPTION OF PREFERRED EMBODIMENTS

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects.

"Treat" as used herein refers to any type of treatment that imparts a benefit to a patient or subject matter as described herein, particularly delaying or retarding the onset or progression of the conditions described herein, or reducing the severity of symptoms, or speeding or improving recovery therefrom.

"Pharmaceutically acceptable" as used herein means that the compound or composition is suitable for administration to a subject to achieve the treatments described herein, without unduly deleterious side effects in light of the severity of the disease and necessity of the treatment.

"Combination" as used herein with respect to a method of administration (e.g., an active compound and an antibiotic administered in combination) includes administering the the two or more compounds simultaneously, or sequentially, sufficiently close in time to produce a combined therapeutic or treatment effect.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S (O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

1. Active Compounds/Active Agents.

Active compounds or active agents of the present invention are, in general, porphyrin compounds. The active compounds include superoxide dismutase (SOD) mimetic prophyrin compounds, and/or redox active porphyrin compounds.

Examples of porphyrin active compounds, and methods of making the same, include but are not limited to those set forth in U.S. Pat. No. 8,470,808 to Piganelli et al.; U.S. Pat. No. 8,183,364 to Batinic-Haberle et al., U.S. Pat. No. 6,916,799 to Fridovich et al.; U.S. Pat. No. 6,479,477 to Crapo et al.; U.S. Pat. No. 6,583,132 to Crapo et al. and in US Patent Application Pub. No. US 2012/0065181 to Warner et al.; the disclosures of which are incorporated by reference herein in their entirety.

Examples of active compounds include but are not limited to compounds of Formula I:

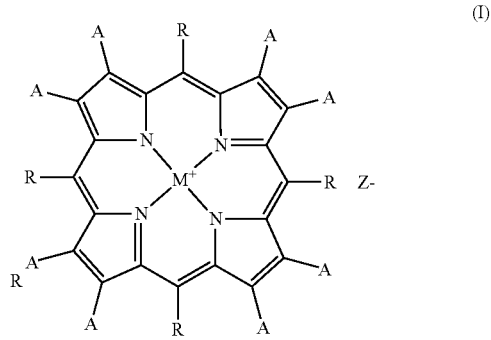

(I)

wherein:

each R is independently substituted or unsubstituted aryl, heteroaryl, cycloalkyl, or heterocycloalkyl;

each A is an independently selected hydrogen, or an electron-withdrawing or electron donating group (e.g., e.g., is halogen, NO$_2$ or CHO), M is a metal, e.g., selected from the group consisting of manganese, iron, copper, cobalt, nickel and zinc, or is absent (in which case a hydrogen is added to each of the two nitrogens required to correct valency), and Z$^-$ is a counterion.

In some embodiments of Formula I above, each R is preferably heteroaryl or heterocycloalkyl, particularly those containing at least one or two nitrogen atoms in the heterocyclic ring (e.g., pyrrolyl, imidazolyl, triazolyl, pyridyl, pyrimidyl, triazinyl, oxazolyl, thiazolyl, oxazinyl, thiazinyl, oxathiazinyl, etc.), in some embodiments wherein at least one of which nitrogen atoms (or in some embodiments at least two of which nitrogen atoms) are optionally but preferably substituted (e.g., quaternized) with a substituent such as described in connection with heterocyclic groups above (e.g., substituted with alkyl, alkoxyalkyl, etc.).

Still more particular examples of the foregoing active compounds include but are not limited to those set forth below.

A. Alkyl Substituted Imidazole Porphyrins.

In some embodiments the active compound has a structure of Formula A1 or A2:

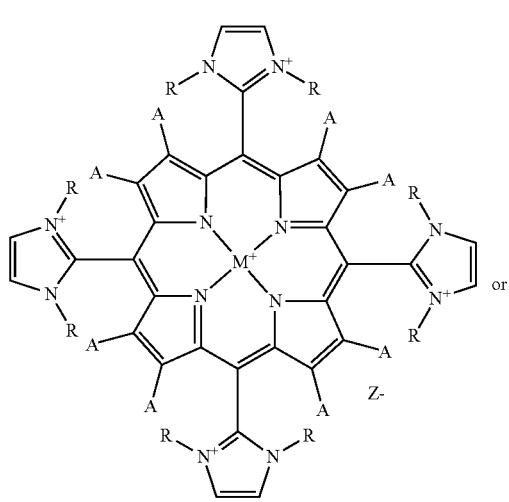

(A1)

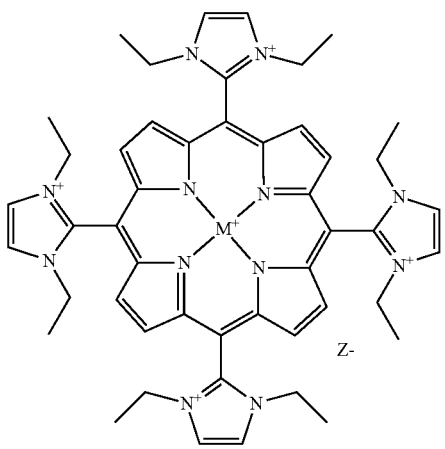

wherein Z– is a counterion.

B. Alkyl Substituted Pyridyl Porphyrins

In some embodiments the active compound has a structure of Formula B1 or B2:

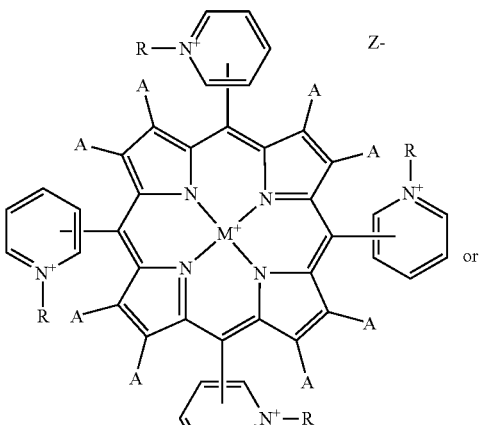

(B1)

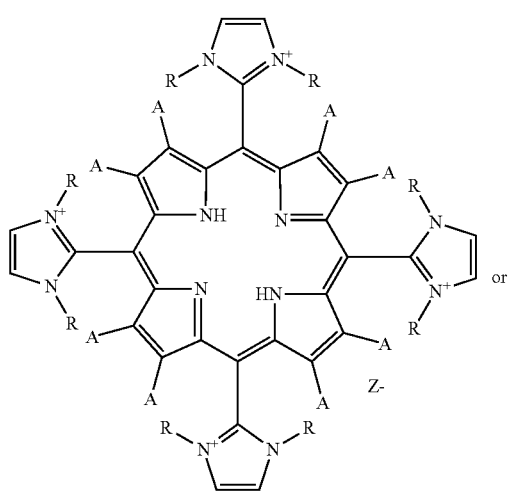

(A2)

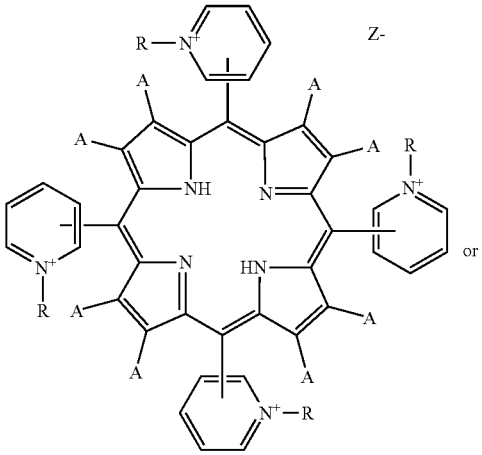

(B2)

wherein:

each R is $C_{1-12}$ alkyl (straight chain or branched), more preferably $C_{2-6}$ alkyl, and most preferably ethyl, propyl, butyl, or pentyl (straight chain or branched);

each A is, independently, hydrogen or an electron withdrawing group (e.g., halogen, $NO_2$ or CHO), M is metal selected from the group consisting of manganese, iron, copper, cobalt, nickel and zinc, and $Z^-$ is a counterion.

In some embodiments the active compound has the formula:

wherein:

each R is $C_{1-12}$ alkyl (straight chain or branched), more preferably $C_{2-6}$ alkyl, and most preferably ethyl, propyl, butyl, or pentyl (straight chain or branched);

each A is, independently, hydrogen or an electron withdrawing group (e.g., halogen, $NO_2$ or CHO), M is metal selected from the group consisting of manganese, iron, copper, cobalt, nickel and zinc, and $Z^-$ is a counterion.

In some embodiments the compound has a structure of the Formula V:

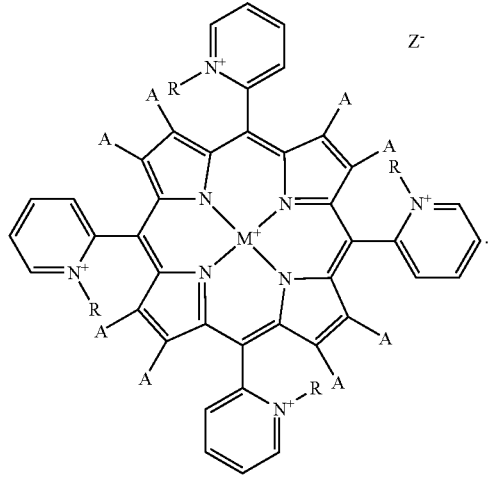

V wherein each R, A, M and Z is as given in connection with Formula B1 and B2 above.

In some embodiments the compound has the structure:

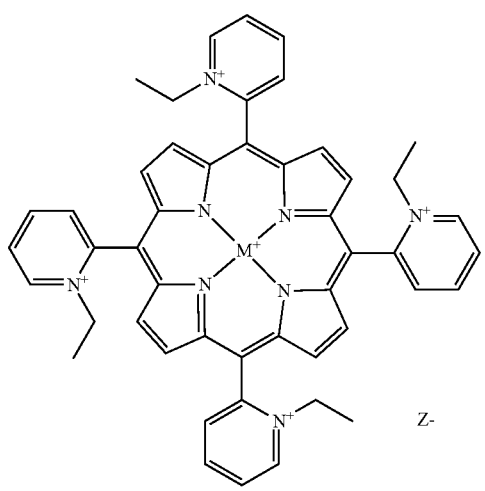

wherein $Z^-$ is a counterion.

C. Alkoxyalkyl Substituted Pyridyl Porphyrins.

In some embodiments the active compound has a structure of Formula C1 or C2:

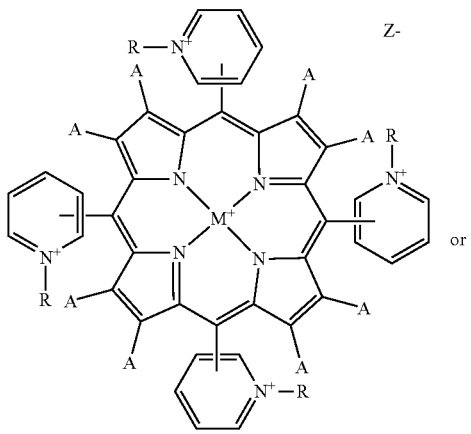

or

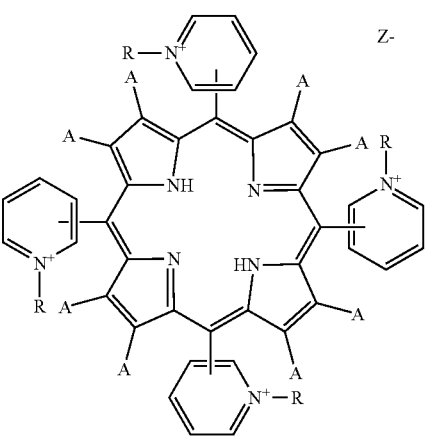

wherein:

each R is $-(CH_2)_m CH_2 OX$;

m is 1 or 2, preferably 1;

X is $C_{1-12}$ alkyl (straight chain or branched), more preferably $C_{2-6}$ alkyl, and most preferably ethyl, propyl, butyl, or pentyl (straight chain or branched).

each A is, independently, hydrogen or an electron withdrawing group (e.g., halogen, $NO_2$ or CHO), M is metal selected from the group consisting of manganese, iron, copper, cobalt, nickel and zinc, and $Z^-$ is a counterion.

In some embodiments the compound has a structure of the Formula V:

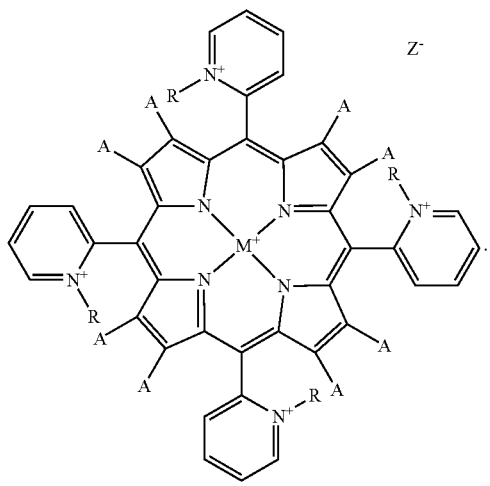

wherein each R, A, M and Z is as given in connection with Formula C1 and C2 above.

In some embodiments the compound has the structure:

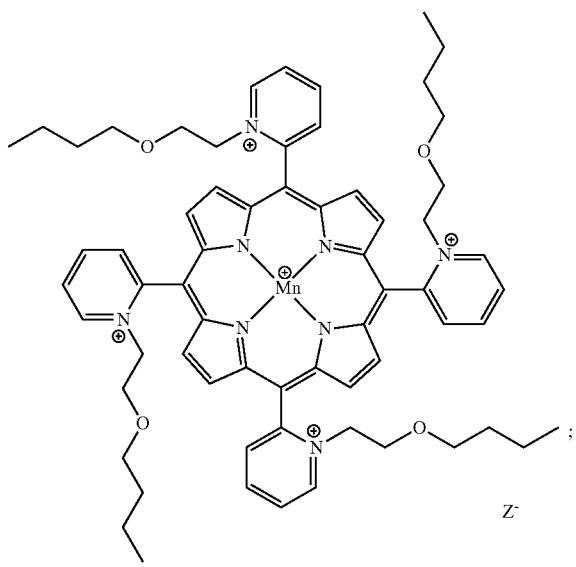

wherein $Z^-$ is a counterion such as chloride (this compound is also referred to as MnTnBuOE-2-PyP$^{5+}$ herein).

D. Salts.

The active compounds disclosed herein can, as noted above, be prepared in the form of their salts or pharmaceutically acceptable salts, e.g., to provide a compound or composition including a counterion as noted above. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques. Of course, the liposomal formulations containing the compounds disclosed herein or salts thereof may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidylcholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multi-dose use. Of course, as indicated, the pharmaceutical compositions of the present invention may be lyophilized using techniques well known in the art.

Topical Formulations.

As noted above, the active compound(s) of this application can be prepared as topical formulations. For a general review of topical formulations see, for example, Topical Drug Delivery Systems: A Review: pharmainfo.net, volume 6(5) 2008, incorporated herein in its entirety. The active compound(s) of this application can be topically formulated for external or internal use. External topicals are spread, sprayed or otherwise dispersed onto cutaneous tissue to cover the affected area. Internal topicals are typically prepared for application to the mouth, vaginal or anorectal tissue.

Topical formulations (or drug delivery systems) are typically classified by their physical state and include: solids, including but not limited to, powders, aerosols, sprays and plasters; liquids, including but not limited to, lotions, liniments, solutions, emulsions, oils, suspensions and aerosols; and semi-solids, including but not limited to, ointments, creams, pastes, gels, jellies and suppositories.

In some embodiments, the carriers and vehicles include, but are not limited to, micro or nanocapsules, nanoemulsions/submicron emulsions/miniemulsions, solid lipid nanoparticles, multiple emulsions, microemulsions. Vesicular carriers include, but are not limited to, liposomes, niosomes, transfersomes, ethosomes, and aquasomes. Chemical penetration enhancers include, but are not limited to, sulfoxides and similar chemicals, azone, pyrrolidones, fatty acids, essential oils terpenes and terpenoids, oxazolidinones, ureas, water, alcohols, fatty alcohols, and glycerols, and surfactants, see, for example, Mathur, V. et al., Physical and chemical penetration enhancers in transdermal drug delivery system, Asian J. Pharm., 4:173-83 (2010) and Escobar-Chavez, J. J. et al in Pharmacology edited by Luca Gallelli (2012) incorporated herein by reference in their entireties.

In some embodiments the topical formulation comprises chemical penetration enhancers. Chemical penetration enhancers include, but are not limited to solvents, surfactants, and chemicals. Examples of solvents include, but are not limited to, water, alcohols such as methanol and ethanol, alkyl methyl sulfoxide, dimethyl sulfoxide, alkyl homologs of methyl sulfoxide such as dimethyl acetamide, and dimethylformamide; pyrrolidones such as 2-pyrrolidone, N-methyl, and 2-pyrrolidone; laurocapran (Azone), propylene glycol, glycerol, silicone fluids and isopropyl palmitate. Examples of surfactants include anionic surfactants including, but not limited to, dioctyl sulphosuccinate, sodium lauryl sulfate and decodecylmethyl sulphoxide; cationic surfactants; and nonionic surfactants such as Pluronic F127 and Pluronic F68. Other chemical penetration enhancers include bile salts such as sodium taurocholate, sodium deoxycholate and sodium tauroglycocholate; binary systems such as propylene glycol/oleic acid and 1,4-butanediol/linoleic acid; and chemicals such as N,N-diethyl-m-toluamide and calcium thioglycolate.

In another embodiment the topical formulation comprises chemical penetration enhancers including, but not limited to N-methyl-2-pyrolidone, glycols such as diethylene glycol, propylene glycol and tetraethylene glycol, fatty acids including, but not limited to, lauric, myristic and capric, nonionic surfactants including, but not limited to, polyoxyethylene-2-oleyl ether and polyoxyethylene-2-stearyl ether. In another embodiment essential oils of eucalyptus, chenopodium and ylang-ylang are used. In one embodiment L-menthol, terpenes, oxazolidinones, and ureas are used as chemical penetration enhancers see, for example, Pathan, I. B. et al., Tropical J. Pharm. Res., 8(2):173-179 (2009).

In other embodiments the topical formulations comprise common topical ingredients that include, but are not limited to, vehicles such as hydrophobic vehicles, water-miscible vehicle co-solvents, structural matrix formers; suspending, jelling, or viscosity inducing agents, water-in-oil emulsifiers, preservatives, and chelating agents.

In some embodiments, hydrophobic vehicles include hydrocarbons such as liquid petrolatum (mineral oil, liquid paraffin, paraffin oil), white petrolatum (petroleum jelly, Vaseline), yellow petrolatum (petroleum jelly), and squalane (perhydrosqualene, spinacane); silicones such as liquid polydimethylsiloxanes (dimethicone, silastic, medical grade silicone oil); alcohols such as lauryl alcohols (1-dodecanol, dodecyl alcohols), myristyl alcohols (tetradecanol, tetradecyl alcohols) cetyl alcohols (hexadecanol, ethal, palmityl alcohols), stearyl alcohols (stenol, cetosteryl alcohols) and oleyl alcohols (ocenol); sterols and sterol esters, including, but not limited to, lanolin (hydrous wool fat, lanum), anhydrous lanolin (wool fat, anhydrous lanum, agnin), and semi synthetic lanolin's; carboxylic acids such as lauric acid, myristic acid, palmitic acid, stearic acid and oleic acid; esters and polyesters including, but not limited to, cholesterol esters (stearate), ethylene glycol monoesters, propylene glycol monoesters, glyceryl monoesters, glyceryl monostearate, sorbitol monoesters, sorbitain monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, and isopropyl palmitate; ethers and polyethers such as polyethylene-polypropylene glycols (pluronics).

In another embodiment, water-miscible vehicle co-solvents include polyols and polyglycols such as propylene glycol (1,2-propanediol), glycerin (glycerol), liquid polyethylene glycol, solid polyethylene glycol (hard macrogol, carbowax) and 1,2-phenols-hexanetriol, sorbitol solution 70%; esters and polyesters such as polyoxyethylene sorbitain monoesters (stearate-tweens) and polyoxy ethylene sorbitan polyesters (tweens); ethers and polyethers, including but not limited to, polyethylene glycol monocetyl ether (cetomacrogol 1000) and polyethylene-polypropylene glycols (pluronics).

In other embodiments, structural matrix formers include but are not limited to hydrocarbons, silicones, polyols and polyglycols, alcohols, sterols and sterol esters, carboxylic acids, esters and polyesters. Examples of hydrocarbons include, but are not limited to, white petrolatum (petroleum jelly, Vaseline), yellow petrolatum (petroleum jelly), paraffin (paraffin wax, hard paraffin), microcrystalline wax and ceresin (mineral wax, purified ozokerite). Examples of silicones include, but are not limited to fumed silica (cab-O-sil), bentonite (colloidal aluminum silicate) and veegum (colloidal magnesium aluminum silicate). Examples of polyols and polyglycols include, but are not limited to solid polyethylene glycol (hard macrogol, carbowax). Examples of alcohols include, but are not limited to, cetyl alcohols (hexadecanol, ethal, palmityl alcohols) and stearyl alcohols (stenol, cetosteryl alcohols). Examples of sterols and sterol esters include, but are not limited to, cholesterol (cholesterin), lanolin (hydrous wool fat, lanum), anhydrous lanolin (wool fat, anhydrous lanum, and agnin), and semi-synthetic lanolin's. Examples of carboxylic acids include, but are not limited to, lauric acid, myristic acid, palmitic acid, stearic acid, and oleic acid. Examples of esters and polyesters include, but are not limited to, bees wax, white bees wax (bleached bees wax), carnauba wax, myricin, cholesterol esters (stearate), polyoxyethylene sorbitain, monoesters (stearate-tweens), lard, and hydrogenated oils.

In another embodiment suspending, jelling or viscosity inducing agents include silicones, polycarboxylates, polysulfates, polysaccharides and other compounds. Silicones include, but are not limited to, uhmed silica (cab-O-sil), bentonite (colloidal aluminum silicate) and veegum (colloidal magnesium aluminum silicate). Polycarboxylates, polysulfates and polysaccharides include, but are not limited to, agar, alginates, carrageen, acacia, tragacanth, methylcellulose, carboxy methylcellulose, hydroxy ethyl cellulose, carboxy vinyl polymer, gelatin, pectin, xanthan, and polyacrylic acid. Other compounds include, but are not limited to, ethanolamine and triethanolamine.

In some embodiments, water-in-oil (w/o) emulsifiers include but are not limited to, sterols and sterol esters, carboxylic acids, ether and polyethers. Sterols and sterol esters include, but are not limited to, cholesterol (cholesterin), lanolin (hydrous wool fat, lanum), anhydrous lanolin (wool fat, anhydrous lanum, agnin), and semi-synthetic lanolin's. Carboxylic acids include, but are not limited to, the $Na^+$, $K^+$ and ethanolamine salts of lauric acid, myristic acid, palmitic acid, stearic acid, and oleic acid. Ethers and polyethers include, but are not limited to, polyethylene-polypropylene glycols (pluronics).

In another embodiment, oil-in-water (o/w) emulsifiers include, but are not limited to, esters and polyesters, ethers and polyethers and other miscellaneous reagents. Esters and polyesters, include, but are not limited to, polyoxyethylene sorbitain monoesters (stearate-tweens), polyoxy ethylene esters (stearate-polyethylene glycol monoesters, Myrj), and polyoxy ethylene sorbitan polyesters (tweens). Ethers and polyethers, but are not limited to, polyethylene glycol monocetyl ether (cetomacrogol 1000) and polyethylene-polypropylene glycols (pluronics). Other miscellaneous reagents, but are not limited to, sodium lauryl sulfate, Borax (sodium borate), ethanolamine and triethanolamine.

In still another embodiment, preservatives include antimicrobials such as benzalkonium chloride, benzoic acid, benzyl alcohol, bronopol, chlorhexidine, chlorocresol, imidazolidinyl urea, paraben esters, phenol, phenoxyethanol, potassium sorbate, and sorbic acid. Preservatives also include antioxidants such as α-tocopherol, ascorbic acid, ascorbyl palmitate, butylated hydroxyanisole, sodium ascorbate, and sodium metabisulfite.

In one embodiment, chelating agents include but are not limited to, citric acid and edetic acid. The chelating agents can be combined with buffers produced from reagents such as phosphoric acid, $NaH_2PO_4$, glycine, acetic acid, triethanolamine and boric acid. In another embodiment, chelating agents can be combined with humectants including, but not limited to, glycerin, propylene glycol, glyceryl triacetate, sorbitol, xylitol, maltitol, polydextrose, quillaia, lactic acid, urea, and lithium chloride.

In one embodiment, ointments comprise active compound(s) in ointment bases. Ointment bases are typically classified by the USP into four general groups (a) hydrocarbon bases including but not limited to, petrolatum, USP; white petrolatum, USP; yellow petrolatum, USP; white petrolatum, USP; (b) absorption bases that include water-in-oil emulsions (c) water-removable bases that include hydrophilic ointment, USP; and (d) water-soluble bases such as polyethylene glycol ointment, NF.

In another embodiment, creams comprise active compound(s) dissolved or suspended in water removable or emollient bases. Creams are classified as water-in-oil or oil-in-water. There are several types of creams including but not limited to cleaning and cold cream or lotion, vanishing and foundation cream, night and massage cream, hand and body cream, all purpose cream, and moisturizing cream. Examples of cream bases include (a) cream base, w/o (rose water ointment) oleaginous phase including but not limited to, spermaceti, white wax, almond oil, sodium borate and an aqueous phase including but not limited to, sodium borate, stronger rose water, NF, and water (b) cream base o/w including an oleaginous phase including but not limited to, stearyl alcohol, beeswax and sorbitan monooleate, and an aqueous phase including but not limited to, sorbitol solution, polysorbate 80, methyl paraben, and water (c) cream base, o/w (vanishing cream) including an oleaginous phase including, but not limited to, stearic acid, stearyl alcohol, cetyl alcohol and an aqueous phase including but not limited to, glycerin, methyl paraben, propyl paraben, potassium hydroxide, and water.

In another embodiment, active compound(s) can be formulated as a paste or gel. Examples of gelling agents include, but are not limited to, synthetic macromolecules such as Carbomer 934 and cellulose derivatives such as carboxymethylcellulose and hydroxypropyl methylcellulose. In one embodiment, gels include single phase and double phase gels.

In one embodiment, active compound(s) can be formulated as a jelly. In one embodiment, jellies are water-soluble bases typically prepared from natural gums such as tragacanth, pectin, alginate and boroglycerin or from synthetic derivatives of natural substances such as methylcellulose and carboxymethylcellulose.

In some embodiments, the active compound(s) can be formulated as a lotion or liniment. Examples of lotions include, but are not limited to, hand lotions, face lotions and body lotions. Lotions can comprise alcohols such as ethyl alcohol, antiseptics, emollients and haemostypic substances. In another embodiment, lotions comprise extract of witchhazel, menthol, glycerin, boric acid, alum, potassium oxyquinoline; sulfate and chloro form.

In one embodiment, active compound(s) can be formulated as a suppository. In some embodiments, suppositories comprise bases including, but not limited to, cocoa butter, glycerin, hydrogenated vegetable oils, and polyethylene glycol.

In some embodiments, the active compound(s) can be formulated as a powder. In another embodiment, powders include, but are not limited to, body powder, dusting powder, talcum powder, face powder, and medicated powders.

In some embodiments, the active compound(s) can be formulated as a solution. In an embodiment, solvents used to prepare solutions include, but are not limited to, water, ethyl alcohol and propylene glycol.

In another embodiment, the active compound(s) can be formulated as an emulsion. In some embodiments, emulsions include, but are not limited to, water-in-oil, oil-in-water, water-in-oil-in-water and oil-in-water-in-oil.

In one embodiment, the active compound(s) can be formulated as a suspension. In some embodiments, suspensions include, but are not limited to, flocculated and deflocculated suspensions.

In some embodiments, the active compound(s) can be formulated in the form of an aerosol. In one embodiment, topical aerosols comprise hydrocarbons (propane, butane and isobutene), and compressed gases such as nitrogen, carbon dioxide and nitrous oxide.

In some embodiments, a healing ointment such as Aquaphor® can be employed in conjunction with the topical formulation. See, U.S. Pat. No. 7,976,854 to Hattendorf et al. incorporated herein in its entirety.

In some embodiments the active compound(s) can be formulated with VersaBase Cream, VersaBase Foam, VersaBase Gel, VersaBase Lotion, or VersaBase Shampoo.

In some embodiments the active compound(s) can be formulated as a spot-on formulation. See, U.S. Pat. No. 7,531,186 to Boeckh et al. incorporated herein in its entirety. In one embodiment, the topical formulation comprises the active compound(s), a liquid carrier vehicle and optionally a crystallization inhibitor. In some embodiments, the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethylene glycol monoethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of ethanol, isopropanol or methanol; and optionally a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

In certain embodiments a topical formulation comprises: an active compound, a pharmaceutically acceptable dipolar aprotic solvent or an acid; and a pharmaceutically acceptable aqueous secondary solvent. See, U.S. Pat. No. 6,844,004 to Anderson herein incorporated by reference. In some embodiments, the acid is a carboxylic acid and is exemplified by acetic acid. In other embodiments, the acid is hydrochloric acid. In some embodiments, the aqueous secondary solvent is a surfactant. Surfactants are well known in the art and are organic lipid compounds that are normally produced by the lung tissue and help with the opening of the alveolar constrictions during breathing. Surfactants are also commercially available. In still other embodiments the aqueous secondary solvent is an aqueous lipid emulsion. The aqueous lipid emulsion can comprise a lipid component that includes at least one vegetable oil and at least one fatty acid. Such a lipid component can comprise at least about 5% by weight soybean oil and at least about 50% by weight fatty acids. In some embodiments, the lipids in the composition are preferably present in a form other than liposomes, for example, at least about 50% by weight of the lipid is not in the form of liposomes, more preferably a least about 75%, and most preferably at least about 95%. In other embodiments the secondary solvent can be water, a saline solution, or a dextrose solution. In some embodiments, the composition further comprises an ointment and/or a cream base. The ointment base can comprise one or more of petrolatum, mineral oil, ceresin, lanolin alcohol, panthenol, glycerin, bisabolol, cocoa butter and the like. The ointment or cream can be any commonly known commercially available ointments or creams such as Aquaphor™ or Eucerin™.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The effective amount (e.g., therapeutically effective or treatment effective amount) or dosage of any specific active compound as described herein, for use in any specific method as described herein, will vary depending on factors such as the condition being treated, the route of administration, the general condition of the subject (e.g., age, gender, weight, etc.), etc. In general (e.g., for oral or parenteral administration), the dosage may be from about 0.01, 0.05, or 0.1 milligram per kilogram subject body weight (mg/kg), up to about 1, 5, or 10 mg/kg. For topical administration, the active agent may be included in a pharmaceutically acceptable composition to be applied in any suitable amount, typically from 0.01, 0.1, or 1 percent by weight, up to 10, 20, or 40 percent by weight, or more, of the weight of the composition, again depending on factors such as the condition being treated, condition of the subject, etc.

The active agents described herein may be administered directly or through the administration to the subject of a pharmaceutically acceptable prodrug which is in turn converted to the active agent in vivo. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

4. Skin Disorders for Treatment.

The present invention may be used to treat a variety of skin disorders, including but not limited to: Acne, Acne Posacea, Drug reaction, Alopecia Areata, Androgenic atopecia, Pseudopelade, Lichen planopilaris, Hemangiomas, Actinic Keratosis, Skin cancer (e.g., Basal cell carcinoma, Squamous cell carcinoma, Bowen's Disease, Melanoma, Merkel cell carcinoma), Sjogren syndrome. Polysarteritis Nodosa, Dermatomyositis, Wegner granulomatosis, Sarcoidosis, Bullous dermatoses, Psoriasis including Inverse psoriasis, Lichen Planus, Keratoacanthoma, Lichen Sclerosis et Atrophicus, Vulvodynia, Diaper Dermatitis, Paget's Disease, Lichen Planus, Lichen Simplex Chronicus, Hidradenitis Suppurative, Fixed Drug Eruption, Familial Benign Pemphigus, Contact Dermatitis, Seborrheic dermatitis, Bullous Dermatoses (including Bullous Pemphigoid, Cicatricial Pemphigoid, Bullous Lupus Erythematosis, Herpes Gestationis, Pemphigus Vulgaris, Paraneoplastic Pemphigus, Pemphigus Foliaceus, Dermatitis Herpetiformis, Linear IgA Dermatosis, Epidermolysis Bullosa Acquisita, etc.), Ichthyoses, Pityriasis Rosea, Transient Acantholytic Dermatosis, Erythema Annulare Centrifugrin, Urticaria, Granuloma Annulare, Erythema Multiforme, Granuloma faciale, Acute febrile dermatosis, Urticarial Vasculitis, Scleroderma, Gout, Decubitus Ulcers, Melasma, Vitiligo, Piebaldism, Panniculitis, Erythema Nodosum, Seborrheic Keratosis, Sebaceous Hyperplasia, Scar, Dermatofibroma, Neurofibromatosis, Connective Tissue Disorders, Eczema, Atopic Dermatitis, Nummular Eczema, Mastocytosis, Cutaneous Infections, or dermatologic complications of infections (e.g., Viral Diseases, Bacterial Diseases, Fungal Disease), Pruritus Gravidarum, Pemphigoid Gestationis, Impetigo Herpetiformis, Lupus Erythematosus, and connective tissue diseases with dermatologic manifestations, Dermatomyositis, Systemic Sclerosis, Eosinophilic Fasciitis, Psoriatic Arthritis, Acanthosis Nigricans, Hypersensitivity reactions, Graft—versus—Host Disease (dermatologic manifestations), etc.

The present invention is explained in greater detail in the following non-limiting Examples. In the examples, "MnTnBuOE-2-PyP$^{5+}$" refers to Manganese ortho tetrakis(N-n-butoxyethylpyridinium-2-yl)porphyrin.

Example 1

Treatment of Psoriasis with MnTnBuOE-2-PyP$^{5+}$

The therapeutic efficacy of MnTnBuOE-2-PyP$^{5+}$ when topically delivered was evaluated in a 38 year old caucasian male with large areas of moderately severe plaque-forming psoriasis on upper and lower portions of both legs, with each involved area being approximately 10-20 cm in diameter. MnTnBuOE-2-PyP$^{5+}$ was formulated in LIPODERM® topical compounding cream base (available from the Professional Compounding Centers of America (PCCA)). at 0.01% and 0.1% concentrations producing a light brown cream which was applied b.i.d. to lesions on one extremity. Marked improvement occurred within 5 days with decreased inflammation, marked decrease in clinical irritation and a decrease in the area of remaining mild psoriatic reaction. Equivalent efficacy was achieved for lesions treated with both 0.01% and 0.1% MnTnBuOE-2-PyP$^{5+}$ in LIPODERM® cream base.

Example 2

Treatment of Psoriatic Involvement of the Scalp with MnTnBuOE-2-PyP$^{5+}$

A second subject, a 70 year old caucasian male, with psoriatic involvement of the scalp of moderate severity was topically treated with MnTnBuOE-2-PyP$^{5+}$0.1% in LIPODERM® cream base twice daily for 3 weeks. Complete resolution of the psoriatic scalp reaction was observed. No return of the psoriatic reaction was observed 30 days after treatment stopped.

Example 3

Preparation of a Topical Emulsion Base (Hydrophilic Ointment)

An emulsion base is prepared with the following ingredients in accordance with known procedures (UNC Eschelman School of Pharmacy, *The Pharmaceutics and Compounding Laboratory, Ointments: Preparation and Evaluation of Drug Release* (1996-2015)):

| Ingredient | Amount by weight |
|---|---|
| Sodium Lauryl Sulfate | 10% |
| Propylene Glycol (SP Gr = 1.035) | 12% |
| Stearyl Alcohol | 25% |
| White Petrolatum | 25% |
| Purified Water | 37% |

The stearyl alcohol and white petrolatum are melted together on a hot plate to 70° C. The remaining ingredients are dissolved in water and the solution is heated to 70° C. The oleaginous phase is added slowly to the aqueous phase, stirring constantly, and the mixture removed from the heat and stirred until it congeals.

Example 4

Preparation of MnTnBuOE-2-PyP$^{5+}$ in a Topical Emulsion Base

MnTnBuOE-2-PyP$^{5+}$ is formulated in the topical emulsion based described in Example 3 by mixing therewith in amounts of at 0.01% and 0.1% by weight. The resulting cream is applied b.i.d. to topical lesions.

Examples 5-6

Preparation of Additional Active Compounds in a Topical Emulsion Base

These examples are carried out in the same manner as described in Example 4 above, except that one or the other of the following two compounds is used in place of MnT-nBuOE-2-PyP$^{5+}$.

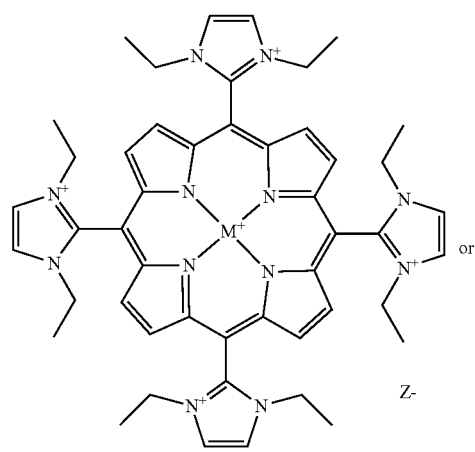

or

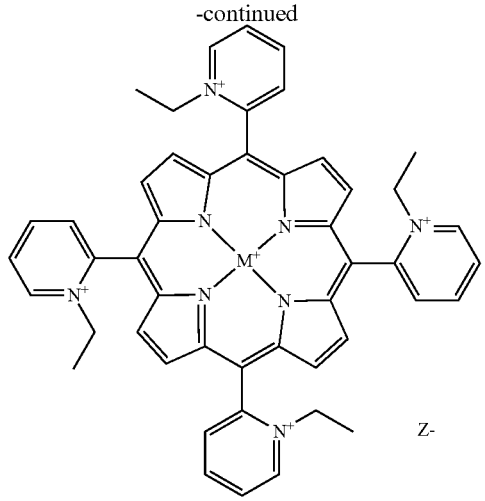

wherein Z– is a counterion such as a chloride ion.

Example 7

Preparation of Hydrophilic Ointment USP

A hydrophilic ointment is prepared with the materials set forth in the Table below:

| Material Name | Quantity/kg (g) |
|---|---|
| Methylparaben | 0.25 |
| Propylparaben | 0.15 |
| Sodium lauryl sulfate | 10 |
| Propylene glycol | 120 |
| Stearyl alcohol | 250 |
| White petrolatum | 250 |
| Water purified | 370 |

The sterayl alcohol and the white petrolatum are melted on a steam bath and warmed to about 75° C. The other ingredients are dissolved in the purified water and warmed to about 75° C. All ingredients are mixed together and stirred until the mixture congeals. See *Handbook of Pharmaceutical Manufacturing, Part II; Formulations of Semisolid Drugs* (CRC Press 2004).8

Example 8

Preparation of MnTnBuOE-2-PyP$^{5+}$ in a Hydrophilic Ointment

MnTnBuOE-2-PyP$^{5+}$ is formulated in the hydrophilic ointment described in Example 7 by mixing therewith in amounts of at 0.01% and 0.1% by weight. The resulting cream is applied b.i.d. to topical lesions.

Examples 9-10

Preparation of Additional Active Compounds in a Hydrophilic Ointment

These examples are carried out in the same manner as described in Example 8 above, except that one or the other of the following two compounds is used in place of MnT-nBuOE-2-PyP$^{5+}$.

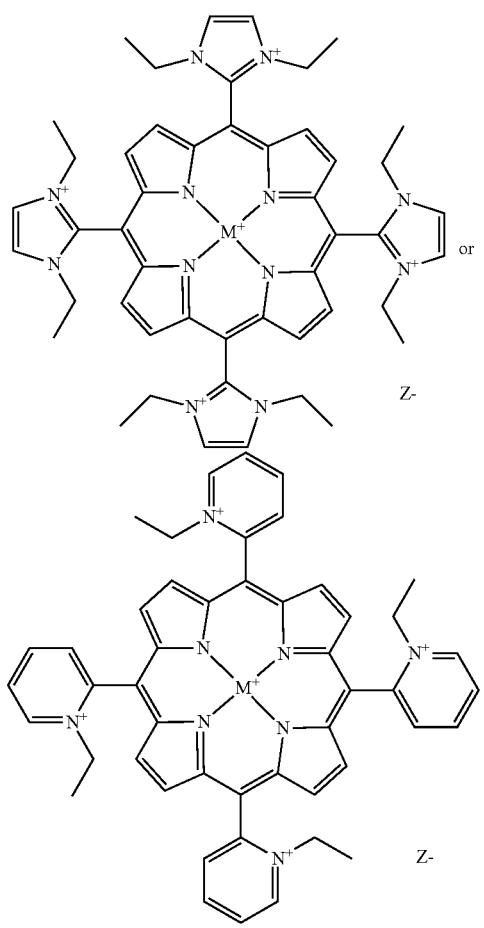

wherein Z– is a counterion such as a chloride ion.

Example 11

Preparation of Base Cream for Extemporaneous Preparations

A base cream is prepared with the materials set forth in the Table below:

| Item | Material name | Quantity/kg (g) |
|---|---|---|
| 1 | Cetylstearyl alcohol | 70 |
| 2 | Cremophor A 6 | 15 |
| 3 | Cremophor A 25 | 15 |
| 4 | Liquid paraffin | 120 |
| 5 | Paraben(s) | 2 |
| 6 | Water | 678-697 |
| 7 | Propylene glycol | 80 |
| 8 | Active ingredient | 0.01 to 2.0 |

A mixture of items 1-5 and the water are heated separately to about 80° C. With rigorous stirring, the water is added to the obtained solution. Items 7 and 8 are heated until the active ingredient is dissolved or suspended therein, then mixed with the aqueous solution, and stirring continued as they are cooled to room temperature, See *Handbook of Pharmaceutical Manufacturing, Part II; Formulations of Semisolid Drugs* (CRC Press 2004). In the alternative, the composition can be prepared without the active ingredient, and the active ingredient added by mixing with the composition after the composition has cooled.

Example 12

Preparation of MnTnBuOE-2-PyP$^{5+}$ in a Base Cream

MnTnBuOE-2-PyP$^{5+}$ is formulated in the hydrophilic ointment described in Example 11 by mixing therewith in amounts of at 0.01% and 0.1% by weight. The resulting cream is applied b.i.d. to topical lesions.

Examples 13-14

Preparation of Additional Active Compounds in a Base Cream

These examples are carried out in the same manner as described in Example 12 above, except that one or the other of the following two compounds is used in place of MnTnBuOE-2-PyP$^{5+}$.

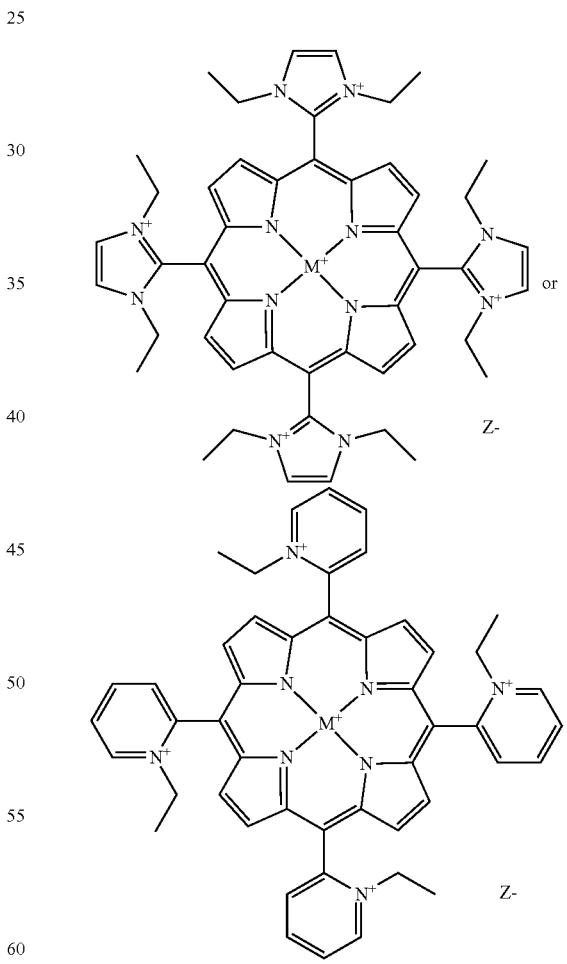

wherein Z– is a counterion such as a chloride ion.

The foregoing is illustrative of the present invention, and is not to be construed as limiting thereof. The invention is defined by the following claims, with equivalents of the claims to be included therein.

That which is claimed is:

1. A method of treating a skin disorder in a subject in need thereof, comprising administering to said subject an active agent in a treatment effective amount, wherein said active agent is a compound selected from the group consisting of Formula A1, Formula B1, and Formula C1:

(A1)

(B1)

(C1)

wherein:

for the compound of Formula A1 or Formula B1 each R is $C_{1-12}$ alkyl, and for the compound of Formula C1 each R is —$(CH_2)_m CH_2 OX$;

m is 1 or 2;

X is $C_{1-12}$ alkyl;

each A is, independently, hydrogen, a halogen, —$NO_2$, or —CHO;

M is a metal selected from the group consisting of manganese, iron, copper, cobalt, nickel and zinc; and $Z^-$ is a counterion;

or a pharmaceutically acceptable salt thereof.

2. The method of claim 1, wherein said skin disorder is an inflammatory or neoplastic skin disease.

3. The method of claim 1, wherein said skin disorder is atopic dermatitis.

4. The method of claim 1, wherein said skin disorder is psoriasis.

5. The method of claim 1, wherein said skin disorder is contact dermatitis.

6. The method of claim 1, wherein said skin disorder is seborrheic dermatitis.

7. The method of claim 1, wherein said skin disorder is acne.

8. The method of claim 1, wherein said skin disorder is selected from the group consisting of radiation-induced skin inflammation, radiation-induced skin fibrosis, radiation-induced oral or gastrointestinal mucositis, basal-cell carcinoma of the skin, squamous-cell carcinoma of the skin, and actinic keratosis.

9. The method of claim 1, wherein said administering step is a systemically or parenterally administering step.

10. The method of claim 1, wherein said administering step is a topically administering step.

11. The method of claim 1, wherein said active compound has the structure:

wherein Z– is a counterion.

12. The method of claim 1, wherein said active compound has the structure:

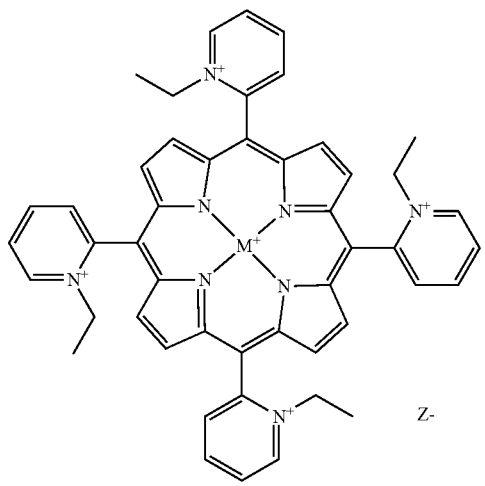

wherein Z⁻ is a counterion.

13. The method of claim 1, wherein said active compound has the structure:

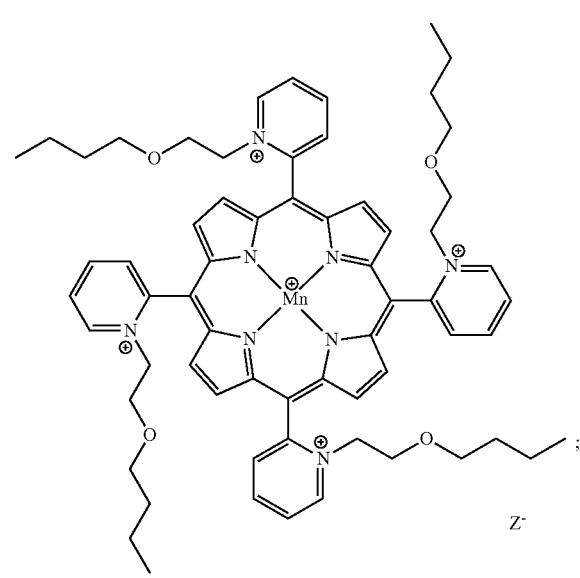

wherein Z⁻ is a counterion.

14. The method of claim 1, wherein said active agent is a compound of Formula A1:

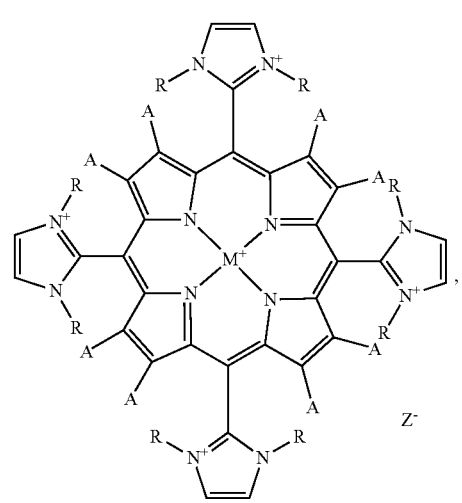

wherein:
 each R is $C_{1-12}$ alkyl;
 each A is, independently, hydrogen, a halogen, —NO$_2$, or —CHO;
 M is a metal selected from the group consisting of manganese, iron, copper, cobalt, nickel and zinc; and
 Z⁻ is a counterion;
or a pharmaceutically acceptable salt thereof.

15. The method of claim 1, wherein said active agent is a compound of Formula B1:

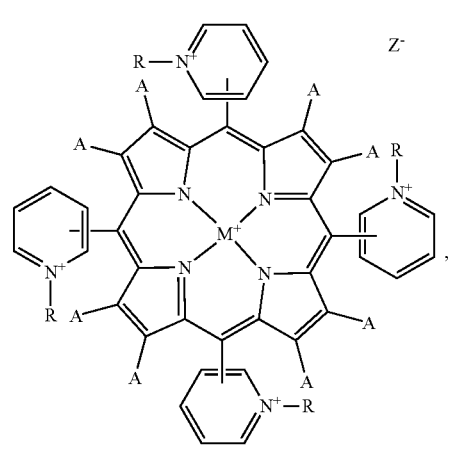

wherein:
 each R is $C_{1-12}$ alkyl;
 each A is, independently, hydrogen, a halogen, —NO$_2$, or —CHO;
 M is a metal selected from the group consisting of manganese, iron, copper, cobalt, nickel and zinc; and
 Z⁻ is a counterion;
or a pharmaceutically acceptable salt thereof.

16. The method of claim 1, wherein said active agent is a compound of Formula C1:

(C1)

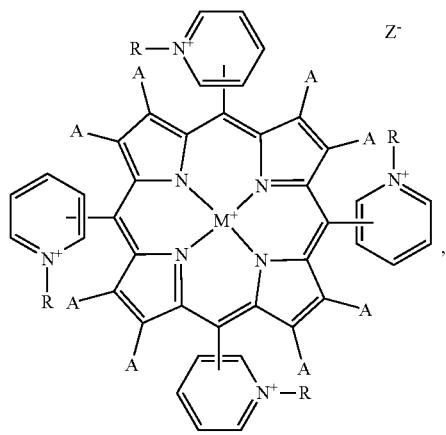

wherein:
each R is —(CH$_2$)$_m$CH$_2$OX;
m is 1 or 2;
X is C$_{1-12}$ alkyl;
each A is, independently, hydrogen, a halogen, —NO$_2$, or —CHO;
M is a metal selected from the group consisting of manganese, iron, copper, cobalt, nickel and zinc; and
Z$^-$ is a counterion;
or a pharmaceutically acceptable salt thereof.

17. The method of claim 1, wherein administering to said subject said active agent comprises administering to said subject a cream comprising said active agent.

* * * * *